United States Patent
Dewing et al.

(10) Patent No.: US 7,145,462 B2
(45) Date of Patent: Dec. 5, 2006

(54) SYSTEM AND METHOD FOR AUTOMATICALLY GENERATING AN ALERT MESSAGE WITH SUPPLEMENTAL INFORMATION

(75) Inventors: Wende L. Dewing, Minneapolis, MN (US); Rand P. Whillock, North Oaks, MN (US)

(73) Assignee: Honeywell International Inc., Morristown, NJ (US)

( * ) Notice: Subject to any disclaimer, the term of this patent is extended or adjusted under 35 U.S.C. 154(b) by 353 days.

(21) Appl. No.: 10/754,409

(22) Filed: Jan. 9, 2004

(65) Prior Publication Data

US 2004/0212505 A1    Oct. 28, 2004

Related U.S. Application Data

(60) Provisional application No. 60/439,346, filed on Jan. 10, 2003.

(51) Int. Cl.
  *G08B 23/00* (2006.01)
(52) U.S. Cl. ............ 340/573.1; 340/628; 340/632; 379/45
(58) Field of Classification Search ............ 340/573.1
See application file for complete search history.

(56) References Cited

U.S. PATENT DOCUMENTS

| | | | |
|---|---|---|---|
| 4,259,548 A | 3/1981 | Fahey et al. | |
| 4,665,385 A | 5/1987 | Henderson | |
| 4,803,625 A | 2/1989 | Fu et al. | |
| 4,952,928 A | 8/1990 | Carroll et al. | |
| 5,045,839 A | 9/1991 | Ellis et al. | |
| 5,086,385 A | 2/1992 | Launey et al. | |
| 5,228,449 A | 7/1993 | Christ et al. | |
| 5,311,185 A | 5/1994 | Hochstein et al. | |
| 5,400,246 A | 3/1995 | Wilson et al. | |
| 5,410,471 A | 4/1995 | Alyfuku et al. | |
| 5,441,047 A | 8/1995 | David et al. | |
| 5,771,001 A | 6/1998 | Cobb | |
| 6,028,514 A * | 2/2000 | Lemelson et al. | 340/539.13 |
| 6,396,403 B1 | 5/2002 | Haner | |
| 6,980,112 B1* | 12/2005 | Nee | 340/573.1 |
| 6,985,771 B1* | 1/2006 | Fischell et al. | 607/3 |
| 2003/0078029 A1* | 4/2003 | Petite | 455/404 |

FOREIGN PATENT DOCUMENTS

| | | |
|---|---|---|
| EP | 0 558 975 A1 | 2/1993 |
| GB | 2285135 A | 6/1995 |
| WO | WO 01/075653 A3 | 10/2001 |

* cited by examiner

*Primary Examiner*—Daniel Wu
*Assistant Examiner*—George A. Bugg
(74) *Attorney, Agent, or Firm*—Kris T. Fredrick (57) ABSTRACT

An automated monitoring and response system includes sensors for monitoring an actor and the actor's environment, and an alert module interfaced with the sensors and adapted to identify an existence of an emergency situation relating to the actor or the environment. The alert module is adapted to generate an alert message for one or more responders, the alert message including a primary alert message component and a supplemental alert message component. The supplemental alert message component includes non-primary supplemental information relating to the actor and/or the environment and giving context to the at least one emergency situation, including, for example, sensor data relevant to the emergency situation.

38 Claims, 4 Drawing Sheets

SYSTEM AND METHOD FOR AUTOMATICALLY GENERATING AN ALERT MESSAGE WITH SUPPLEMENTAL INFORMATION

CROSS-REFERENCE TO RELATED APPLICATIONS

This application is entitled to the benefit of, Provisional Patent Application Ser. No. 60/439,346, filed Jan. 10, 2003; and is related to all of the following; Non-Provisional patent application Ser. No. 10/286,398, filed Nov. 1, 2002; Non-Provisional patent application Ser. No. 10/341,335, filed Jan. 10, 2003; Non-Provisional patent application Ser. No. 10/339,941, filed Jan. 10, 2003; Non-Provisional patent application Ser. No. 10/444,514, filed May 23, 2003; and Non-Provisional patent application Ser. No. 10/703,097, filed Nov. 6, 2003; the teachings of all of which are incorporated herein by reference.

BACKGROUND OF THE INVENTION

The present invention relates to a system and method for generating an alert message relating to an actor in an environment. More particularly, it relates to a system and method that automatically generates an emergency situation alert message including supplemental information that informs a responder receiving the alert message as to a context of the emergency situation.

A number of different electronic-based devices are currently available to individuals that automatically generate and send an alert message in response to a potential emergency situation. As used throughout this specification, an "emergency situation" is defined as any event that causes an actor to require or desire assistance, regardless of severity or whether the need for assistance is actual or perceived. For example, home security systems notify or alert a designated responder of possible problems, such as a broken window or unexpected movements. Similarly, personal assistant devices such as panic buttons or fall sensors carried by an actor send an alert message to a designated responder when activated. The format of the alert message generated by these and other devices can vary, ranging from a simple electronic signal that prompts an alarm device (e.g., flashing light or audible warning) at the responder's location, to automatically placing a telephone call to the responder (or other designated parties) with a pre-recorded message that an alarm has been triggered at the actor's home. Regardless, the responder is provided with only limited information relating to the situation, at best consisting of notification that an emergency situation possibly exists, a basic emergency type classification (e.g. fire, security, medical), the actor's name, and the address of the actor's home, with the name and address information being expressly stated in the message or implied by the responder upon referencing the origination point of the message signal with internal records.

Clearly, notifying a designated responder of a potential emergency situation is of primary importance. Unfortunately, however, the limited information associated with current alarm messages does not allow the responder to evaluate the potential emergency situation in advance, or prepare and execute a most appropriate response strategy. This is problematic at several levels. For example, an alarm message from a panic button-type device gives no information as to what is the exact problem. Similarly, a fall-type sensor device may indicate that the actor has fallen, but does not give any information as to what caused the actor to fall. Under these scenarios, the designated responder can do nothing more than arrive at the actor's home as soon as possible, a task sometimes complicated by the responder not being informed of a best route. Further, without any information that gives context to places the potential emergency situation, a responder receiving the alert message may not fully understand the severity of a particular situation. For example, a certain actor may have a history of repeatedly requesting assistance via their alarm device (e.g., panic button) under circumstances that do not otherwise constitute an "emergency". Without knowing the context of a newly issued alarm message/request, the responder may, based upon past history, unintentionally deem the new alarm as being of less importance and thus may not sufficiently respond to an actual emergency event. This same concern arises in the context of home security systems, where false alarms are common.

A related concern associated with available alarm devices is an inability to confirm that an alarm message has been received and is being acted upon. Existing devices do nothing more than send an alert message. In certain instances, however, the designated responder may be unavailable or otherwise not receive the alert message, for example due to a failure in the communication link. Similarly, where the alert message is a pre-recorded message delivered via telephone, the so-delivered message may be received by an answering machine or similar device. Under these circumstances, the pre-recorded message may not include enough information for the responder to later understand or respond to the potential emergency situation. Regardless, because existing devices do not confirm that the alert message has been received, let alone perform secondary response plans in the event the alert message has not been received or is not being acted upon, the emergency situation may go entirely unaddressed.

Existing electronic alert devices and systems are of great value, and provide users with a strong sense of security. Unfortunately, parties assigned with the task of responding to an alert message are unable to fashion a most appropriate response strategy in advance of responding due to a lack of information relating to a context of the situation. Further, existing technology cannot confirm that an alert message has been received. Therefore, a need exists for a system and method of automatically generating an alert message that includes both primary and supplemental information components that allow the designated responder to prepare and execute a more informed response. Preferably, the system and method is adapted to confirm receipt of an alert and that a response is forthcoming.

SUMMARY OF THE INVENTION

One embodiment of the present invention is an automated monitoring and response system that includes sensors for monitoring an actor and the actor's environment, and an alert module interfaced with the sensors and adapted to identify an existence of an emergency situation relating to the actor or the environment. The alert module is further adapted to generate an alert message for one or more responders, the alert message including a primary alert message component and a supplemental alert message component. The primary alert message component includes information for enabling a response to the at least one emergency situation, such as:

an indication that the at least one emergency situation exists, a location of the at least one emergency situation, a basic emergency type classification for the at least one emergency situation, and actor identification information.

The supplemental alert message component, on the other hand, includes non-primary supplemental information relating to the actor and/or the environment and giving context to the at least one emergency situation.

DETAILED DESCRIPTION OF THE PREFERRED EMBODIMENT

Figure 1:
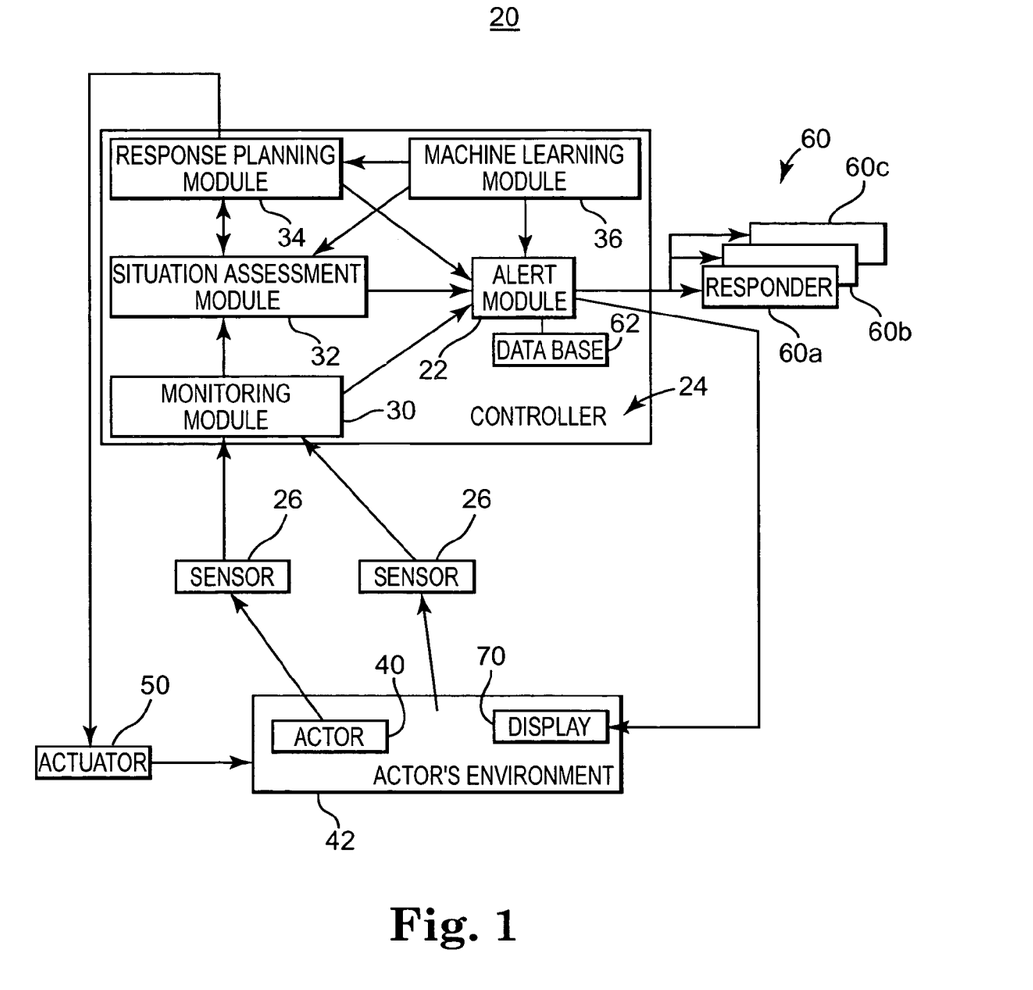
FIG. 1 is a block diagram illustrating an alert system in accordance with the present invention.

The present invention relates to a system and method of generating an alert message relating to an actor in a daily living environment as part of the operation of an automated monitoring and response system. In this regard, FIG. 1 provides an exemplary illustration, in block form, of a monitoring and response system 20 including an alert module 22 in accordance with the present invention. The system 20 can assume a variety of forms, but preferably includes a controller 24 and a plurality of sensors 26. As described in greater detail below, the controller 24 preferably further includes other components such as a monitoring module 30, a situation assessment module 32, and a response planning module 34. In general terms, the sensors 26 actively, passively, or interactively monitor activities of an actor 40 as well as segments of an environment 42 of the actor 40. Information or data from the sensors 26 is signaled to the controller 24 for interpretation by the monitoring module 30. The situation assessment module 32 processes information from the monitoring module 30 to determine what the actor 40 is doing (and/or intending to do), along with what is happening in the actor's environment 42. The response planning module 34, in turn, generates appropriate responses that can be carried out via other devices, such as one or more actuators 50. The alert module 22 reviews information generated by the monitoring module 30 and/or the situation assessment module 32, and operates to identify emergency situations relating to the actor 40 and/or the actor's environment 42. Upon identifying an emergency situation, the alert module 22 further functions to generate an alert message consisting of primary and supplemental information, as described below. The alert message is delivered to one or more designated responders indicated at 60a–60c and collectively, at 60.

The key component associated with the system 20 of the present invention resides in the alert module 22 as described below. As such, the sensors 26, the actuators 50, as well as other modules (e.g., the monitoring module 30, the situation assessment module 32, and the response planning module 34) can assume a wide variety of forms.

In one embodiment, the sensors 26 are networked by the controller 24. The sensors 26 can be non-intrusive or intrusive, active or passive, wired or wireless, physiological or physical. In short, the sensors 26 can include any type of sensor that provides information relating to the activities (or non-activities) of the actor 40 or other information relating to the daily living environment 42. For example, the sensors 26 can include motion detectors, pressure pads, door latch sensors, panic buttons, toilet-flush sensors, microphones, cameras, fall-sensors, door sensors, heart rate monitor sensors, blood pressure monitor sensors, glucose monitor sensors, moisture sensors, a medication caddy, light level sensors, water flow sensors, telephone sensors, thermal sensors, optical sensors, seismic sensors,. etc. In addition, one or more of the sensors 26 can be a sensor or actuator associated with a device or appliance used by the actor 40, such as a stove, oven, television, telephone, security pad, medical dispenser, thermostat, etc., with the sensor or actuator providing data indicating that the device or appliance is being operated by the actor 40 (or someone else).

The controller 24 is preferably a microprocessor-based device capable of storing and operating the various modules illustrated in FIG. 1, including the alert module 22. In one type of embodiment, one or more of the modules 30–34 of the controller 24 are implemented as physically separate components interfaced with one another, each component including electrical/electronic hardware and/or software. In another type of embodiment, one or more of the modules are implemented in computer-readable media as computer software designed around fulfilling their respective designated function.

In another embodiment, one or more of the modules 30–34 are a grouping or inter-working of several individual modules or components that, when operated by the controller 24, serve to accomplish the designated function. In yet another embodiment, separate modules are provided for individual subject matters that internally include the ability to perform one or more of the functions associated with the monitoring module 30, the situation assessment module 32, the response planning module 34, as well as other functions desired for the monitoring and response system 20. Regardless of exact configuration, however, the modules 30–34 serve to monitor information provided by the sensors 26, assess the current situation of the actor 40 and/or the actor's environment 42, generate appropriate interactive plans responsive to the determined situation, and effectuate those plans (relative to the actor 40 and/or anything in the environment 42) via the actuators 50. One embodiment of the controller 24 includes additional features such as an ability to determine intended actions of the actor 40, evaluate system operations based upon unobserved actions of the actor 40, store data logs, provide machine learning capabilities (such as via a machine learning module shown at 36 in the FIG. 1), etc. A more detailed explanation of appropriate system configuration and operation is provided, for example, in patent application Ser. No. 10/341,335, filed Jan. 10, 2003, the teachings of which are incorporated herein by reference.

With the above general explanation of the monitoring and response system 20 in mind, the alert module 22 performs specific functions relating to potential emergency situations. More particularly, the alert module 22 is adapted to identify the existence of a possible emergency situation, formulate an appropriate alert message, and deliver the alert message to the responder 60. Protocol(s), algorithm(s), and/or reference information relating to these functions are stored in a database 62 maintained by the alert module 22 and/or by other database(s) maintained by the controller 24. In a preferred embodiment, the alert module 22 is further adapted to confirm that the responder 60 has received the alert message, and formulate/effectuate alternative alert and response plans in response to the confirmation (or lack thereof).

Identification of a potential emergency situation can be performed by the alert module 22 pursuant to a variety of different parameters, all of which fall under the scope of the present invention. The emergency situation identification can be dictated by activation of a single sensor component (e.g., a panic button, fall sensor, smoke detector, etc.). In another embodiment, the alert module 22 is programmed or adapted to identify a potential emergency situation based upon sensory or user input information provided by multiple sensors 26. In one such embodiment, the identification of a potential emergency situation is based upon a comparison between a measured sequence of sensor events and a pre-determined reference sequence of sensor events. In another such embodiment, a more complex evaluation is performed whereby the alert module 22 infers the existence of an emergency situation based on circumstantial units of information about the actor 40 or the environment 42. For example, in one embodiment, the alert module 22 is programmed such that whenever water flow is detected in the actor's 40 shower for an extended period of time (e.g., greater than 20 minutes) alone or in conjunction with a sensed force on the shower's floor, the alert module 22 makes an inference that the: actor 40 has fallen in the shower and thus that an emergency situation exists.

In another example embodiment, the alert module 22 infers an emergency situation based upon an evaluation of various units of information from multiple data sources (e.g., the actor 40 is diabetic, known to be in the environment 42, a required insulin injection has not be administered, and no movement has been detected for an extended period of time; it can be inferred that the actor 40 is possibly unconscious). With this more complex inference approach, the alert module 22 can rely upon information about the actor 40 stored in the database 62 or in another database maintained by the controller 24, sensory data gathered by one or more sensors 26 in the environment 42, one or more situational assessments made by the situation assessment module 32, and/or upon historical information about the actor's 40 activity or the status of the environment 42 stored in the database 62 or in another database maintained by the controller 24.

In one embodiment, the alert module 22 is programmed or adapted to utilize information generated by the machine learning module 36 to understand the actor's 40 normal routine, in order to identify unusual variations from the routine. In another embodiment, the emergency identification function is performed by the situation assessment module 32 in the manner described above. In another embodiment, the alert module 22 is provided as part of the situation assessment module 32 and/or as part of the response planning module 34 as described in greater detail below, or as part of a domain agent.

Figure 2:
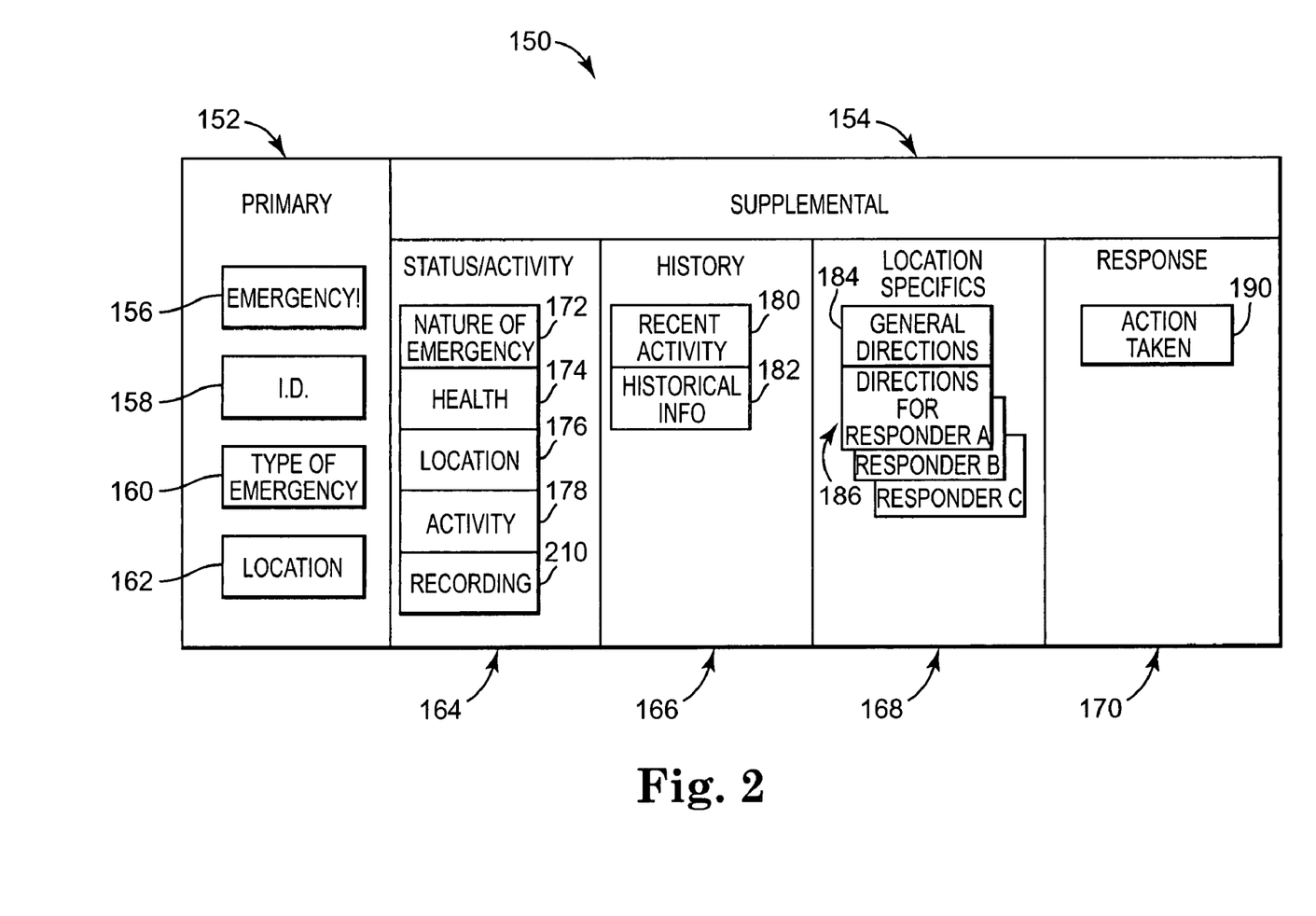
FIG. 2 illustrates an alert message including primary and supplemental alert message components according to one embodiment of the present invention.

Regardless of how emergency situations are identified, the alert module 22 then functions to generate an alert message. FIG. 2 illustrates one embodiment of an alert message 150. The alert message 150 consists of a primary message component 152 and a supplemental message component 154. The primary message component 152 is akin to the message information (or "primary" information) commonly provided by existing alert devices. Namely, the primary information consists of: 1) an identification 156 that an emergency situation exists, 2) the actor's identification 158, such as the actor's name, 3) a classification of the emergency type 160 (e.g., fire, medical, security, etc.), and 4) the current location 162 of the emergency (e.g., the address of the environment 42).

With additional reference to FIG. 1, the supplemental message component 154 includes supplemental information that augments or gives context to the primary information, and in particular the emergency situation. Unlike existing standalone alarm devices, the alert module 22 has access to, and can evaluate information from, all of the sensors 26 and/or the modules 30–34, making generation of the supplemental information possible.

The supplemental information can include a wide variety of different information presented in a number of different formats. In general terms, however, the supplemental message component 154 can include information from one or more of four classes of information, including: 1) status/activity information 164 indicating actor/environment status or actor activity information, 2) historical record information 166, 3) static location specific information 168, and 4) system response information 170. The supplemental message component 154 can include information from one or more, including all, of these classes of information 164–170.

The status/activity supplemental information 164 includes anything that is known about the actor's 40 and/or the environment's 42 current situation. For example, in one embodiment of the alert message 150, the status/activity information 164 can include nature of emergency details 172 on what caused the emergency situation, current health information 174 regarding the actor's 40 current health, current location information 176 on the actor's 40 current location within the environment 42, and the actor's 40 current/recent activity 178.

In one embodiment, the alert module 22 references sensor information (either directly or through other system components, such as the monitoring module 30 and/or the situation assessment module 32) to determine what happened to the actor 40 and/or where the actor 40 is currently located in the actor's environment 42, and then provide this information, as part of the supplemental message component 154 (e.g., primary information of "help needed at 1 Main Street" is supplemented with supplemental information of "actor has fallen down and is apparently unconscious in the basement"). Similarly, the alert module 22 can review sensor information and data libraries to provide specific medical information and/or inferences (e.g., primary message of "help needed at 1 Main Street" is supplemented with supplemental information of "the actor has fallen, the glucose monitor shows abnormal levels, it is believed that the actor did not take an insulin shot as required, it is believed that the actor ate one hour ago, and there is a note from the actor's caregiver that the actor likes to eat high-sugared items").

In another embodiment, the alert module 22 references other modules (such as the situation assessment module 32) for information relevant to the particular emergency situation to include in the status/activity supplemental information 164. For example, the alert module 22 can "classify" the subject matter of the emergency situation (e.g., health related, problems with environment, etc.) and then, based on this classification, utilize pre-determined protocols for designating relevant actor status/activity information 164 (e.g., for health related situation, the alert module 22 is adapted to retrieve information relating to any recent medications taken or food ingested by the actor 40).

The historical record information 166 that can be provided as part of the supplemental message component 154 in one embodiment includes historical information that may be useful to the responder 60. For example, this historical record information can be recent activity information 180 such as the time the actor 40 last ate or what medications they recently took. Additionally, older historical record information 182 can be provided, such as indicating if and when a similar emergency event occurred (e.g., noting that "a similar event occurred last month on the $9^{th}$") In this regard, according to one embodiment, the alert module. 22 maintains historical information in the database 62, or can retrieve desired historical information from one or more other databases maintained by the controller 24.

The static location specific information 168 encompasses a wide variety of potentially useful information about the environment 42. In one embodiment, location specific information 168 includes general directions to the environment 42 and distinguishing features of the environment (e.g., a house color). In another embodiment, location specific information 168 includes responder-specific information, such as specific directions 186 to the environment 42 from each designated responder's default location. In another embodiment, location specific information 168 includes a return phone number identifying other emergency contact responders, and specific information about the actor 40 (e.g., "help needed at 1 Main Street which is a white house one block west of the intersection of First and Main; the 89-year-old actor has fallen down the stairs"). This information is preferably generated and stored by the system 20 (such as in the database 62 maintained by the alert module 22) during initial installation/configuration of the system 20, and updated as necessary.

The system response supplemental information 170 relates to one embodiment in which the monitor and response system 20 is adapted to provide a specific response to an emergency situation (in addition to sending of the alert message), such as by the response planning module 34. In one embodiment, the supplemental information 154 included with the alert message 150 can, with such an installation, describe what the system 20 is doing in response to the alert. For example, in one embodiment, the supplemental information component 154 includes any actions taken description 190 of actions taken by the system 20 in response to an emergency situation. The actions taken description 190 can inform a designated responder 60 that the system 20 has already notified a neighbor or that the system 20 has tried to contact a relative and was unsuccessful. As further examples, the actions taken description 190 can include a statement that the front porch lights at the environment 42 are being flashed so as to assist the responder 60 in finding the environment 42; that a stove has been turned off; etc.

In view of the above, the supplemental information message component 154 can include a number of useful items. In furtherance of providing useful information to designated responders, embodiments of the alert module 22 according to the present invention are adapted to reason about the particular emergency situation and determine what supplemental information will be most useful to the responder 60. In one such embodiment, the alert module 22 includes in the supplemental message component 154 any information used to establish or determine that an emergency situation has occurred or is occurring.

Figure 3:
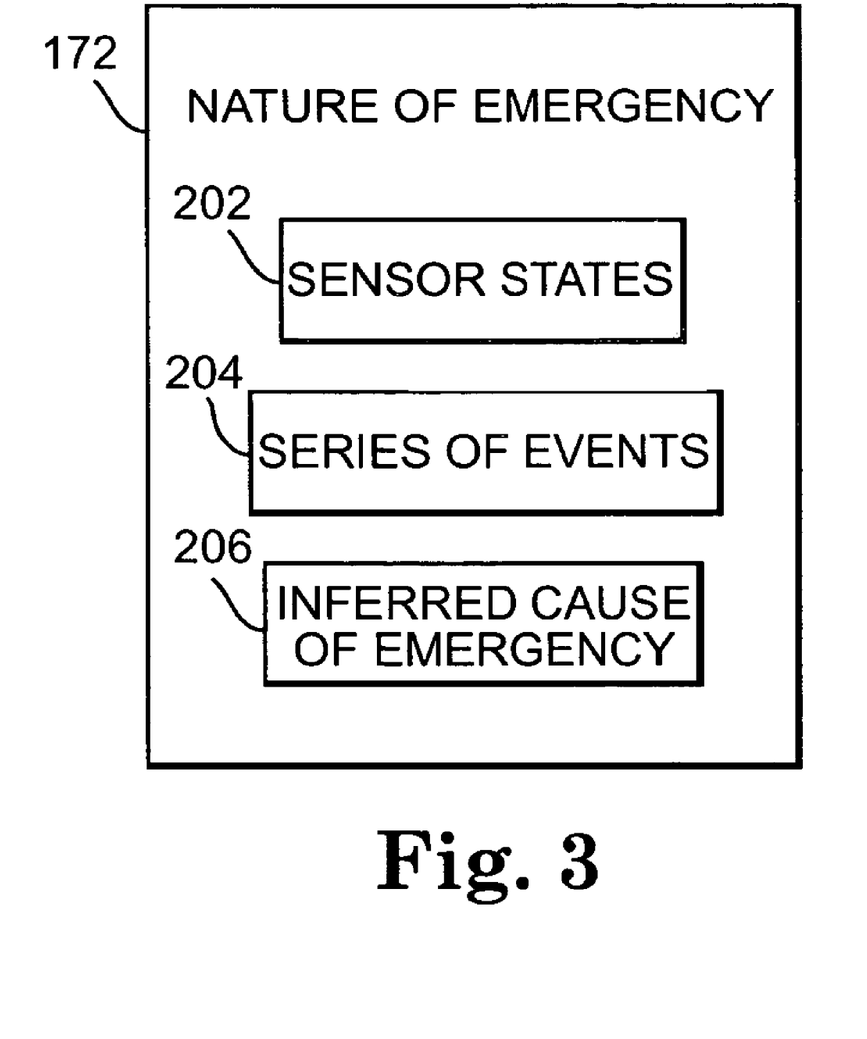
FIG. 3 illustrates one embodiment of a portion of a secondary alert message component that indicates a nature of an emergency situation according to one embodiment of the present invention.

FIG. 3 illustrates one embodiment of the nature of emergency details 172, which are a part of the supplemental information component 154 of the alert message 150. In this embodiment, the nature of emergency details 172 include any sensor state information 202 forwarded by the monitoring module 30 and information assessing a series of events 204 leading up to the emergency situation forwarded by the situation assessment module 32. For example, in one embodiment, the nature of emergency details 172 includes sensor state information 202 identifying specific sensor outputs (e.g., the carbon monoxide sensor in the upstairs hallway is sensing a dangerous level of carbon monoxide). In another embodiment, the alert module 22 interprets the sensor information and provides an assessment of a series of events 204 based on the sensor state information 202 as part of the supplemental information component 154.

In one embodiment, the nature of emergency details 172 includes an inferred cause of emergency message 206 indicating the result of an analysis made by monitoring and response system 20 as to the cause of the emergency situation, based on the sensor states 202 and the series of events information 204. In one embodiment, the alert module 22 includes as the nature of emergency details 172 any information that contributed to the assessment that an emergency situation occurred, plus any actor status, historical record, and/or static environment information that occurred close in time to the event but was not otherwise used to determine the existence of the emergency situation.

Returning to FIGS. 1 and 2, for communicating information about the actor 40 and/or environment 42, the monitoring and response system 20 is, in one embodiment, adapted such that the actor 40 (or another person) can designate certain information, otherwise stored in database(s) of the system 20, as private. Under these circumstances, the so-designated private information will not be included with the supplemental message.

Further, in another embodiment, the alert module 22 is adapted to recognize two or more essentially simultaneous emergency situations and forward relevant information for all situations with a single alert message 150.

In one embodiment, the format of the supplemental message component 154 is optimized by the alert module 22, providing information from a number of different sources. For example, the supplemental message component 154 can include all available sensor information associated with the environment 42 for a predetermined amount of time prior to occurrence of the emergency situation (e.g., a threshold of five minutes can be established such that the supplemental information includes all sensor information generated during the five minutes immediately preceding occurrence of the emergency situation). To this end, depending upon the number of sensors available, the alert module 22 can select and send information only from those sensor(s) of primary relevance (e.g., located in an area of the environment 42 when the emergency situation occurred/is occurring).

In addition to sensor data, assessment information and/or database information, one or more of the supplemental message component categories 164–170 can be augmented by a recording 210 (shown in FIG. 2 for the status/activity information class 164, it being understood that the recording 210 can be associated with other(s) of the classes 166–170). In one embodiment, the alert module 22 is adapted to make an audio and/or video recording 210 and include the recording 210 as part of the supplemental alert message component 154. For example, recording 210 can be a voice message from the actor 40 upon occurrence of the emergency situation. Similarly, where a video camera is provided in the environment 42 and is, as determined by the alert module 22, positioned in an area of the environment 42 where the emergency situation is occurring, the recording 210 can include a video segment from that camera from a short time immediately preceding the emergency situation occurrence.

In another embodiment, the monitoring and response system 20 is adapted to provide and support an actor-specific webpage. In such an embodiment, the alert module 22 is adapted to provide the supplemental message component 154 (and the primary message component 152) on this webpage, and instruct the responder 60, via the alert message 150, to access this webpage for more information regarding the emergency situation. In another embodiment, the alert module 22 is adapted to prompt the display of the supplemental message component 154 (and, where desired, the primary message component 152) at a display monitor (referenced at 70 in FIG. 1) located in the actor's environment 42. With this embodiment, where the responder 60 requests a third party to visit the actor's environment 42 in response to the emergency situation, the third party will have ready access to the supplemental information.

The alert module 22 can employ one or more different protocols for determining the appropriate responder(s) 60 for receiving the alert message. For example, in a simplified embodiment where only one responder has been designated, the alert module 22 simply forwards the alert message 150 to the designated responder 60. Alternatively, in a more robust embodiment, a number of available responders 60a–60c are designated (with their contact information being stored, for example, in the database 62). In this embodiment, the alert module 22 is configured to select one or more of these available responders 60a–60c based upon the particular emergency situation.

For example, in conjunction with designated protocol constraints, where the particular event represents a highly dangerous situation (e.g., a fire at the environment 42 and the actor 40 being incapacitated), in one embodiment, the alert module 22 sends the alert message to all the available responders 60a–60c. Where the event is less problematic and/or calls for a specialized response (e.g., the actor 40 has taken an incorrect medication dosage), in one embodiment, the alert module 22 is configured to send the alert message to less than all of the designated responders 60a–60c.

To this end, in one embodiment, the database 62 is formatted to include a prioritized list of potential responders, their contact information and their schedules. Before sending the alert message 150, the alert module 22 cross-checks the event time, date, and day of week with the stored responder information to determine responder availability. In another embodiment, the database 62 includes a capability rating for each responder relative to certain events (e.g., medical, fire, mental health, etc.). Under these circumstances, the alert module 22 selects the highest priority responder rated for the type of event that has occurred and/or which responder 60 is scheduled to be in communication range with the system 20 at the time of the emergency. In other embodiments, responder prioritization is learned, configured a priori, or queried in real time (e.g., ask the actor 40 whom they would prefer to have the alert message sent to).

In one embodiment of the monitoring and response system 20, the alert module 22, either alone or with another module(s), is configured to select supplemental information content and format based upon the particular responder(s) 60 that are selected to receive the alert message. Potential responders will vary greatly in terms of technological and response capabilities. For example, the responder 60a can be a next-door neighbor or relative that can only receive telephonic messages and provide a limited response (e.g., walking to the actor's environment 42 to check on the actor 40). The alert module 22 is aware of these limitations (for example, via a database stored by the alert module 22), and provide the alert message 150 in an audible, voice form and include supplemental details of relevance to the responder 60a (e.g., the actor has fallen in an upstairs bedroom after taking a bath, but would not include additional details of the actor's blood pressure changes over the past three days as the responder 60a of this example is not trained to understand or interpret this information, thus having the responder 60 review this information adds no value and would only delay the response).

Conversely, a more technologically advanced (though with little medical or other response training/expertise) responder 60b can receive other message formats (e.g., video segments, internet messages, etc.). Similarly, a specialized responder 60c, such as a caregiver, physician, security provider, rescue station, etc., will be provided with additional details regarding the emergency situation context. In short, this embodiment of the alert module 22 is adapted to be aware of capabilities of all available responders, and generate/deliver an alert message that is most appropriate for each responder.

In addition to generating appropriate primary and supplemental information as part of an alert message, the alert module 22 in one embodiment is adapted to monitor a status of the alert message 150 and actions of the responder 60. In particular, because the alert module 22 is adapted to reason in real-time, in one such embodiment, the alert module 22 further requests a response from the responder 60 that has otherwise been provided with the alert message 150. The alert module 22 can simply await acknowledgement by the responder 60 that the alert message has been received. In an alternative embodiment, the alert module 22 is adapted to prompt other actions. For example, the alert module 22 can specifically ask the responder 60 for further instructions, and then act accordingly (e.g., where the emergency situation is the actor 40 falling and the alert message 150 is sent to a neighbor, the alert module 22 is adapted to further ask the neighbor if an ambulance should be called). To this end, where the alert module 22 is adapted to wait for a response from the responder 60, in one embodiment the alert module 22 is further adapted to determine if the alert message 150 was received by a person or by an answering machine. If received by an answering machine, the alert system 22 tailors the alert message 150 in response to suit the situation (e.g., the supplemental information 154 includes the time and date of a call as well as information about what the system 20 will do next; the alert module 22 then tries another contact phone number to get a live person that will acknowledge the alert).

Figure 4:
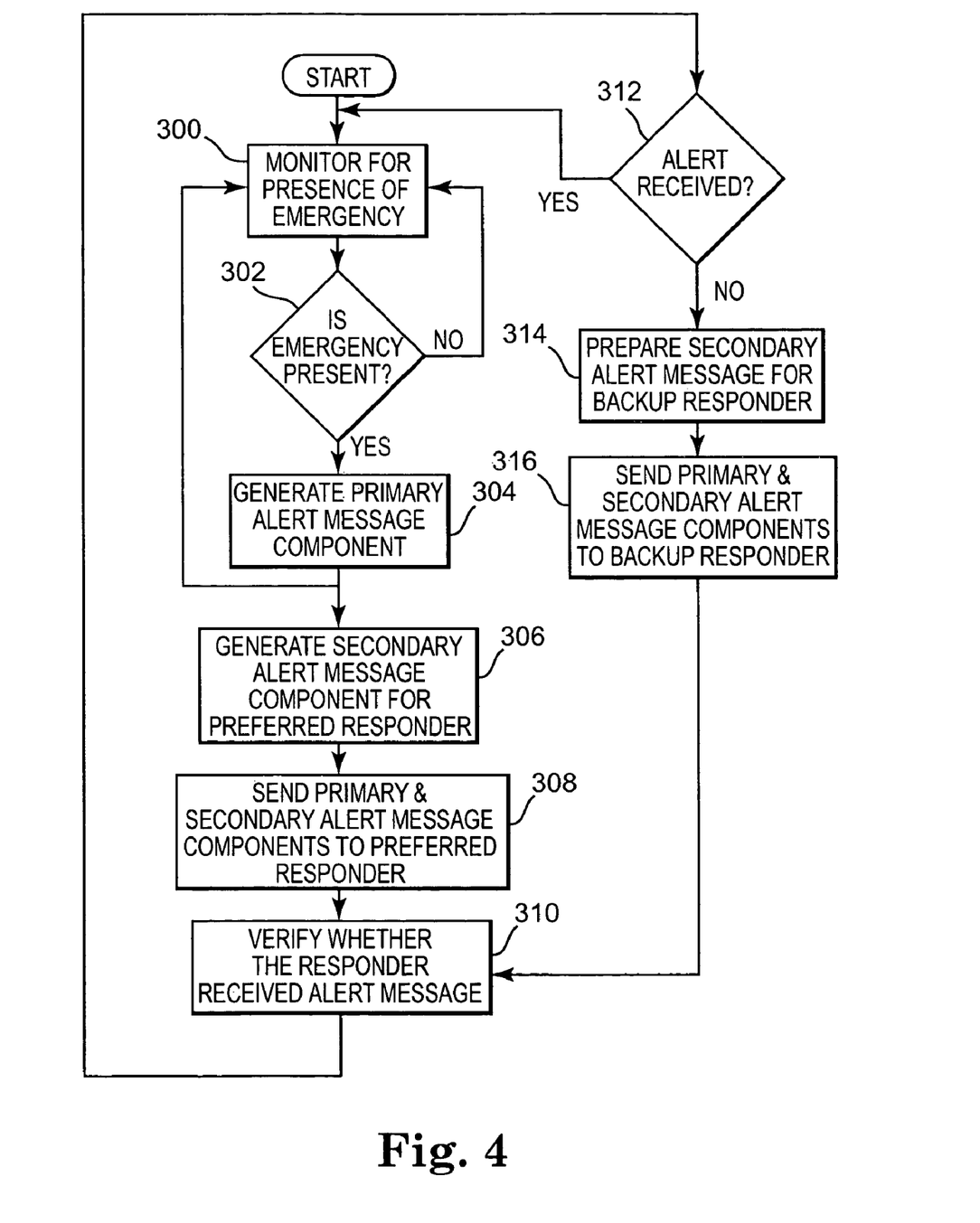
FIG. 4 is a flow diagram illustrating a process of sending an alert message to a preferred responder and backup responders, if necessary, according to one embodiment of the present invention.

FIG. 4 is a flowchart illustrating a process of delivering an alert message to a first designated responder and, if necessary, to one or more backup responders. With additional reference to FIG. 1, at 300, the monitoring and response system 20 operates in its normal regime of monitoring for the presence of emergencies. For example, the controller 24 periodically polls the sensors 26 via the monitoring module 30, and provides the sensory data to the alert module 22 and the situation assessment module 32 for analysis. The alert module 22 tests whether the sensory data is indicative of an emergency situation at 302. If an emergency situation is evident from the sensor readings, the alert module 22 proceeds to generate an alert message, as described below. If no emergency is evident from the sensor readings, the alert module 22 analyzes the situation assessment module's 32 output, together with the sensory data provided by the monitoring module 30, and with static and historic data from the database 62 for any indications of emergency. As described above, in one embodiment the alert module 22 is adapted to make inferences as to the presence of emergencies based on sensory, situation assessment, and historical data. If no emergency situation is evident expressly or inferentially from the available data, the monitoring, analysis, and testing for emergencies processing indicated at 300 and 302 continues repeatedly.

If, at 302, the alert module 22 identifies the presence of an emergency situation, the alert module 22 generates an alert message by generating the primary alert message component at 304, and the secondary the alert message component at 306. Next, at 308, the alert module 22 sends the alert message to a preferred responder, such as responder 60c. In one embodiment, the secondary alert message component is prepared especially for the responder 60c and delivered according to a previously determined protocol implemented by the alert module 22 for the responder 60c. At 310, the alert module 22 verifies if the responder 60c received the alert message in one embodiment, verification 310 is performed according to previously determined protocol. In another embodiment, verification 310 is performed by a second communication initiated by either the alert module 22, or by the responder 60a. At 312, the alert module 22 decides whether the alert message has been successfully delivered to the responder 60. In one embodiment, the alert module 22 allows a certain amount of time to receive verification from the responder 60a before concluding that the delivery of the alert message has failed.

If the alert message has been received by the responder 60, the monitoring and response system 20 returns to its normal (non-emergency) operating mode at 300 and 302 for monitoring the actor and detecting further possible emergencies. If, however, the responder 60 did not receive the alert message, the alert module 22 selects a backup responder, such as responder 60b. At 314, the alert module 22 prepares a secondary alert message component for the responder 60b. Preparation 314, in one embodiment, includes generating a new secondary alert message component especially for the responder 60b and different from the secondary alert message component generated at 306. In another embodiment, preparation 314 includes using the same secondary alert message component as generated at 306. In another embodiment, the alert module 22 determines the contents needed for the secondary alert message component to be delivered to the responder 60b, and generates a new and different secondary message component for the responder 60b only if the contents need to be different from those of the secondary alert message component generated for the responder 60a. At 316, the alert module sends the primary alert message component generated at 304 and the secondary alert message component generated at 314 to the backup responder 60b.

The alert module 22 then proceeds to verify, at 310, the backup responder's 60b receipt of the alert message. If, at 312, the result of verification indicates failure of such receipt, then a second backup responder, such as responder 60c, is selected, and a secondary alert message component is prepared for the secondary backup responder 60c at 314 in a similar procedure as used for preparing the secondary alert message component for backup responder 60b.

Although the present invention has been described with reference to preferred embodiments, workers skilled in the art will recognize that changes can made in form and detail without departing from the spirit and scope of the present invention.

What is claimed is:

1. A method of providing an alert message relating to an actor in an environment with an automated monitoring and response system, the method comprising:
    (a) providing at least one sensor;
    (b) storing facts about at least one of the actor and the environment;
    (c) identifying an existence of at least one emergency situation relating to the actor or the environment, wherein identifying includes evaluating sensory data provided by the at least one sensor located in the environment in conjunction with the stored facts;
    (d) generating a primary alert message component of primary information for enabling a response to the at least one emergency situation, wherein the primary alert message component includes:
        an indication that the at least one emergency situation exists,
        a location of the at least one emergency situation,
        an emergency type classification, and
        actor identification information;
    (e) automatically generating a supplemental alert message component comprising non-primary supplemental information relating to the actor and/or the environment and giving context to the at least one emergency situation; and
    (f) electronically sending the primary and supplemental alert message components to at least one designated responder.

2. The method of claim 1, wherein the supplemental information includes data generated by the at least one sensor.

3. The method of claim 2, wherein a plurality of sensors are provided in the environment, and further wherein the supplemental information includes data generated by at least two of the plurality of sensors.

4. The method of claim 1, wherein the supplemental information includes status information of the actor.

5. The method of claim 4, wherein the status information includes information indicating at least one state of the actor selected from the group consisting of current health, current location in the environment, current activity, and recent activity.

6. The method of claim 1, wherein the supplemental information indicates an inferred cause of the at least one emergency situation based on an assessed status of the actor.

7. The method of claim 1, wherein the supplemental information includes an indication of a series of events leading to the at least one emergency situation.

8. The method of claim 1, wherein the supplemental information includes historical record information.

9. The method of claim 1, wherein the supplemental information includes static environment specific information.

10. The method of claim 1, wherein the supplemental information includes information relied upon for the identifying of the existence of the at least one emergency situation.

11. The method of claim 1, further comprising:
    formulating a response plan for responding to the at least one emergency situation.

12. The method of claim 11, wherein the supplemental information includes the response plan.

13. The method of claim 11, wherein formulating the response plan includes selecting at least one responder from a plurality of designated responders.

14. The method of claim 13, wherein formulating the response plan further includes:
  after selecting the at least one responder, automatically preparing the supplemental information content and/or formatting based upon at least one property of the selected responder selected from the group consisting of location, availability, response capability, technological capability, information access authorization, and training/expertise.

15. The method of claim 1, further comprising:
  verifying whether the at least one designated responder has received the sent alert message components.

16. The method of claim 1, wherein identifying the existence of the at least one emergency situation includes:
  assessing a current situation of the actor and/or the environment based on sensory data provided by the at least one sensor located in the environment; and
  comparing the assessed current situation against at least one reference situation representing a predefined emergency situation, wherein a similarity between the current situation assessment and the at least one reference situation is indicative of an existence of an emergency situation.

17. The method of claim 1, wherein identifying the existence of the at least one emergency situation includes:
  inferring the existence of the emergency situation from circumstantial information about the actor and/or the environment.

18. The method of claim 1, wherein the supplemental information includes a segment of video generated by a camera located in the environment.

19. The method of claim 1, wherein the supplemental information includes a segment of recorded audio.

20. An automated monitoring and response system, comprising:
  sensors for monitoring an actor and the actor's environment; and
  an alert module interfaced with the sensors and adapted to identify an existence of at least one emergency situation relating to the actor or the environment and to generate an alert message for at least one responder;
  wherein the alert message includes a primary alert message component and a supplemental alert message component;
  wherein the primary alert message component comprises primary information for enabling a response to the at least one emergency situation, the primary information including:
    an indication that the at least one emergency situation exists,
    a location of the at least one emergency situation,
    a basic emergency type classification for the at least one emergency situation, and
    actor identification information;
  wherein the supplemental alert message component comprises non-primary supplemental information relating to the actor and/or the environment and giving context to the at least one emergency situation, and includes data from at least two of the sensors.

21. The automated monitoring and response system of claim 20, wherein the alert module is further adapted to identify an emergency situation relating to the actor or the environment and send the alert message to at least one designated responder.

22. The automated monitoring and response system of claim 20, wherein the supplemental information includes status information of the actor including at least one state of the actor selected from the group consisting of current health, current location in the environment, current activity, and recent activity.

23. The automated monitoring and response system of claim 20, wherein the alert module is adapted to infer a cause of the at least one emergency situation, and wherein the supplemental information includes an indication of the inferred cause.

24. The automated monitoring and response system of claim 20, wherein the supplemental information includes historical record information.

25. The automated monitoring and response system of claim 20, wherein the supplemental information includes static environment specific information.

26. The automated monitoring and response system of claim 20, wherein the alert module is adapted to generate the supplemental information to include information relied upon for the identifying of the existence of the at least one emergency situation.

27. The automated monitoring and response system of claim 20, wherein the alert module is adapted to generate the supplemental information to include information based on sensory data gathered close in time to the occurrence of the emergency situation.

28. The automated monitoring and response system of claim 27, wherein the alert module is adapted to limit the information based on sensory data included in the supplemental information to information determined to be relevant to the emergency situation.

29. The automated monitoring and response system of claim 20, wherein the alert module is further adapted to:
  assess the nature of each emergency; and
  generate the supplemental information according to selected of a plurality of protocols based on nature of the emergency.

30. The automated monitoring and response system of claim 20, wherein the alert module is further adapted to formulate a response plan for responding to the at least one emergency situation and further wherein the supplemental information includes the response plan.

31. The automated monitoring and response system of claim 30, wherein the response plan is formulated for at least one responder selected from a plurality of designated responders, and further wherein the alert module is adapted to form the response plan based on at least one criteria selected from the group consisting of nature of the emergency situation, inferred nature of the emergency situation, designated responder priority classification, the actor's responder preferences, designated responder availability; and a capability rating of each designated responder.

32. The automated monitoring and response system of claim 20, wherein the alert module is further adapted to formulate the supplemental information based upon at least one responder property selected from the group consisting of location, availability, response capability, technological capability, information access authorization, and training/expertise.

33. The automated monitoring and response system of claim 20, wherein the alert module is further adapted to verify whether the at least one designated responder has received a sent alert message.

34. The automated monitoring and response system of claim 20, wherein the alert module is further adapted to compare sensory data provided by the sensors against a reference sequence of sensor events representing a predefined emergency situation, and identify an existence of at least one emergency situation when sensory data coincides with the reference sequence of sensor events.

35. The automated monitoring and response system of claim 20, and further comprising:
a situation assessment module interfaced with the alert module and adapted to assess a current situation of the actor and/or the environment based on data provided by the sensors;
wherein the alert module is adapted to compare the assessed current situation against at least one reference situation representing a predefined emergency situation; and
wherein the alert module is adapted to identify an existence of at least one emergency situation when there is similarity between the current situation assessment and the at least one reference situation.

36. The automated monitoring and response system of claim 20, and further comprising:
a database interfaced with the alert module for storing facts about the actor and/or environment;
wherein the alert module is adapted to access the facts as part of identifying the existence of the at least one emergency situation.

37. The automated monitoring and response system of claim 36, wherein the database is adapted to store sensory data from the sensors, and further wherein the alert module is adapted to determine which of the sensor data relates to the at least one emergency situation, and wherein the supplemental information includes the sensor data determined to be related to the at least one emergency situation.

38. A method of providing an alert message relating to an actor in an environment with an automated monitoring and response system, the method comprising:
(a) providing at least one sensor;
(b) identifying an existence of at least one emergency situation relating to the actor or the environment;
(c) generating a primary alert message component of primary information for enabling a response to the at least one emergency situation, wherein the primary alert message component includes:
an indication that the at least one emergency situation exists,
a location of the at least one emergency situation,
an emergency type classification, and
actor identification information;
(d) automatically generating a supplemental alert message component comprising non-primary supplemental information relating to the actor and/or the environment and giving context to the at least one emergency situation, wherein the supplemental information includes a segment of recorded audio; and
(e) electronically sending the primary and supplemental alert message components to at least one designated responder.

* * * * *